United States Patent [19]

Meitzler et al.

[11] Patent Number: 4,733,556
[45] Date of Patent: Mar. 29, 1988

[54] METHOD AND APPARATUS FOR SENSING THE CONDITION OF LUBRICATING OIL IN AN INTERNAL COMBUSTION ENGINE

[75] Inventors: Allen H. Meitzler, Ann Arbor; George S. Saloka, Canton, both of Mich.

[73] Assignee: Ford Motor Company, Dearborn, Mich.

[21] Appl. No.: 945,278

[22] Filed: Dec. 22, 1986

[51] Int. Cl.[4] ............................................. G01N 33/30
[52] U.S. Cl. .......................................... 73/64; 340/631
[58] Field of Search ............... 73/64; 340/603, 631; 324/61 R

[56] References Cited

U.S. PATENT DOCUMENTS

| | | |
|---|---|---|
| 3,971,250 | 7/1976 | Taylor . |
| 4,007,629 | 2/1977 | Hochstein ........................ 73/64 X |
| 4,122,707 | 10/1978 | Leunig .......................... 73/118 R |
| 4,344,322 | 8/1982 | Plapp ........................... 73/118 R |
| 4,377,851 | 3/1983 | McNamara ....................... 364/571 |
| 4,414,847 | 11/1983 | Kohama et al. ............... 73/118 R X |
| 4,443,754 | 4/1984 | King ............................. 73/64 X |
| 4,646,070 | 2/1987 | Yasuhara et al. ................ 73/64 X |

FOREIGN PATENT DOCUMENTS 0080632 11/1982 European Pat. Off. .
0121739 3/1984 European Pat. Off. .

*Primary Examiner*—Stewart I. Levy
*Assistant Examiner*—Joseph W. Roskos
*Attorney, Agent, or Firm*—Paul K. Godwin, Jr.; Clifford L. Sadler

[57] ABSTRACT

An on-board sensor system which compares the dielectric properties of lubricating oil in an internal combustion engine with the dielectric properties of unused oil in a contained volume and providing an output signal indicative of the changes in viscosity correlated to the dielectric constant changes of the lubricating oil.

10 Claims, 5 Drawing Figures

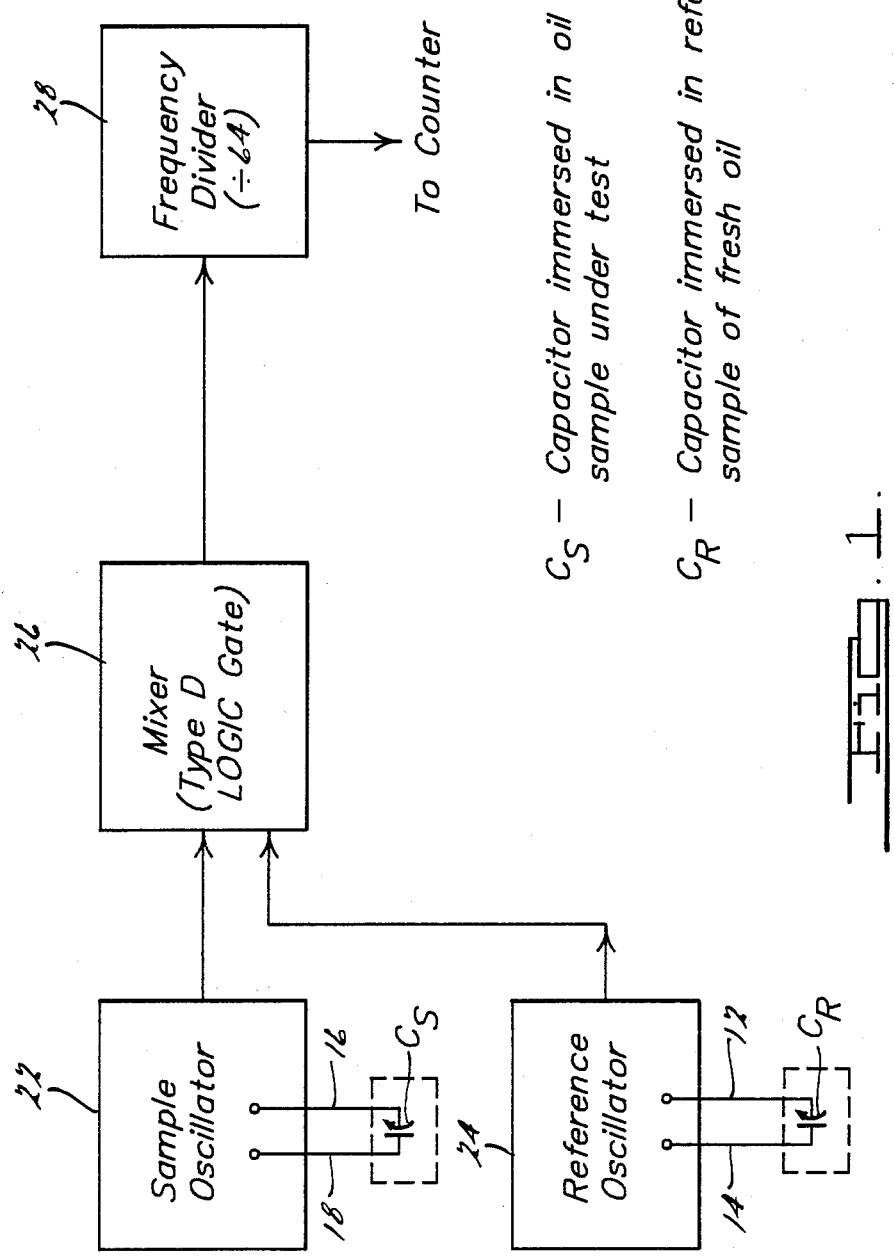

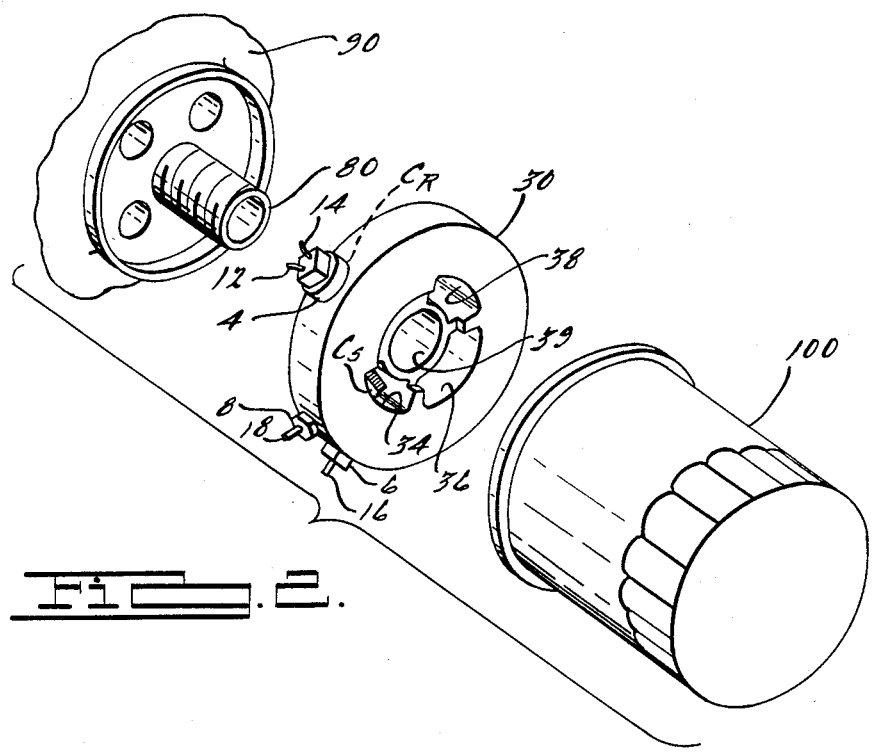
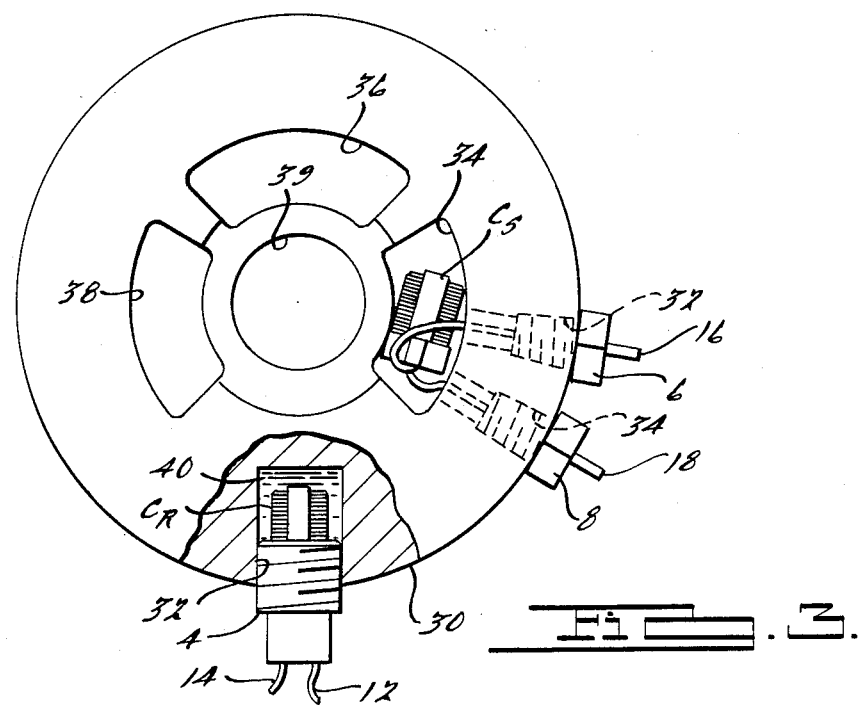

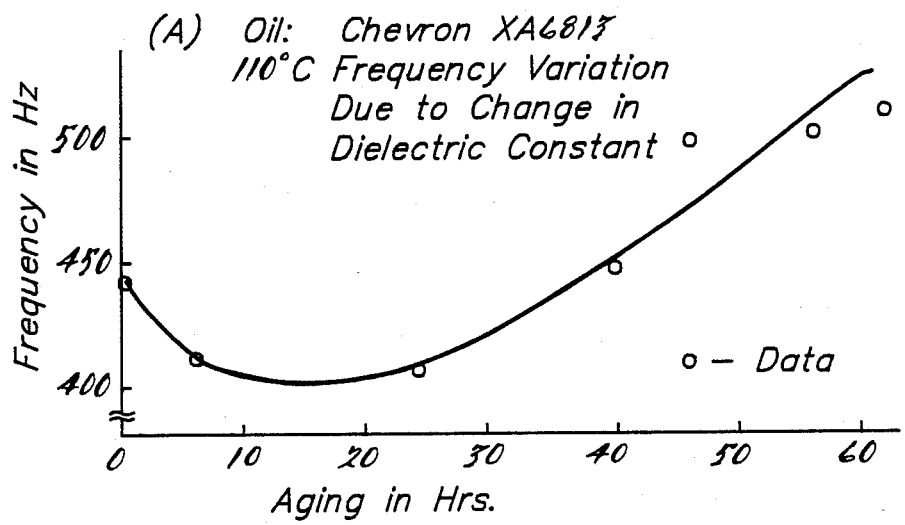
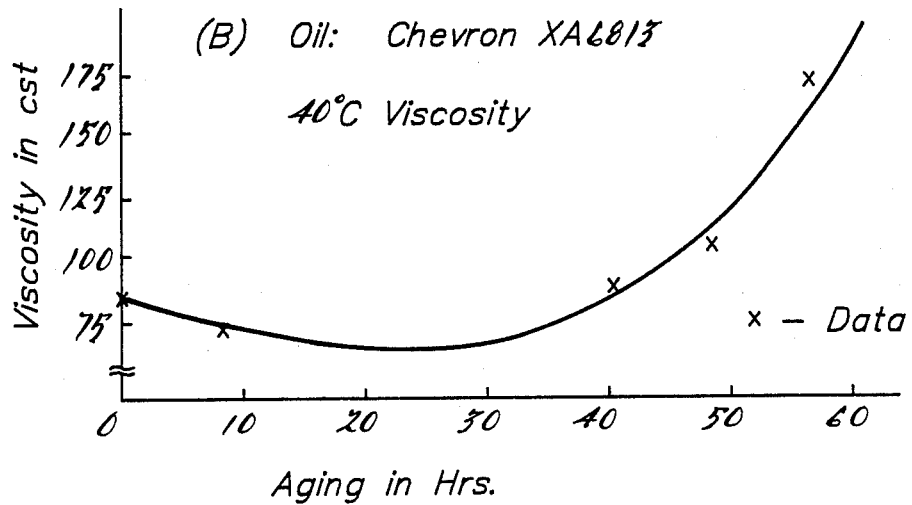

METHOD AND APPARATUS FOR SENSING THE CONDITION OF LUBRICATING OIL IN AN INTERNAL COMBUSTION ENGINE

BACKGROUND OF THE INVENTION

1. Field of the Invention

The present invention is directed to the field of determining the appropriate time to change lubricating oil in internal combustion engines and more specifically to an on-board method and apparatus for directly measuring the change in the engine oil condition.

2. Description of the Prior Art

Currently, in many automotive applications, only the pressure of the lubrication system during engine operation or the level of the oil within the sump prior to engine operation are measured on-board a vehicle. The necessity of changing oil is normally communicated to the vehicle operator via the operator's manual and is based upon the measured use of the vehicle rather than the actual condition of the oil. That adherence to the estimated deterioration of the oil based upon measured use of the vehicle (mileage) is adequate for most engine or vehicle usage. However, when an inferior grade of oil is substituted or the engine is operated in harsh environments the proper interval for oil replacement should be considerably shortened to avoid engine wear. Accordingly, it is desirable to provide an on-board system which directly measures a performance-related property of the oil and provides an indication when the usefulness of the oil as an engine lubricant has deteriorated past a certain level.

U.S. Pat. No. 4,443,754 describes a method for determining the minimum lubricating oil-film thickness within an operating engine by measuring electrical capacitance. In that patent, one of the main bearings of the engine is electrically isolated from the engine block and a capacitance signal is developed between the crankshaft and the isolated bearing so that the entire bearing acts as one plate of a capacitor and the crankshaft acts as the other plate of a capacitor. The degradation of the oil to the point of having a minimum film thickness allows the two plates of the capacitor to become closer together and the electrical capacitive properties to change. The decreased thickness is most likely due an increase in viscosity which, in turn, prevents the oil from flowing between the plates of the capacitor. A circuit is employed which allows the capacitor to be pulsed and monitored until the minimum thickness level is detected.

European Patent Application Publication No. 80632 describes an apparatus that detects the degree of deterioration of lubricating oil by measuring the dielectric constant of the lubricating oil. In that apparatus, a pair of spaced-apart electrodes are immersed in lubricating oil to form a sensor capacitor, the capacitance of which varies as a function of the dielectric constant of the lubricating oil. The sensor capacitor is placed in the oil flow system of the engine so that the oil will flow between the plates of the capacitor. The sensor capacitor is electrically connected in series with another capacitor having a fixed capacitance value to form a voltage divider. AC voltage applied across the divider is divided at a ratio determined by the dielectric constant of the lubricating oil so that the AC voltage across the sensor capacitor is substantially proportional to the engine oil dielectric constant.

European Patent Application Publication No. 121739 also describes a method and apparatus for performing the evaluation of dielectric substances such as lubricating oil. In that publication, an electrical capacitive device having at least a pair of electrodes is disposed in contact with the dielectric substance and a power supply is used for apply a pulse voltage to the electrodes. A current detector is connected to the other side of the capacitor for detecting a transient response current flowing between the electrodes that is dependent upon the component of the dielectric substance disposed between the electrodes. A signal processor is used for evaluating the performance of the dielectric substance based upon the peak value of the transient response current.

SUMMARY OF THE INVENTION

The present invention is intended to provide a method and apparatus for directly measuring the condition of lubricating oil in an internal combustion engine by directly measuring the dielectric properties of the oil experiments indicate that there is a strong correlation between the time variation with usage of oil dielectric constant and oil viscosity.

It is another object of the present invention to compare the dielectric properties of the lubricating oil in an engine with those of unused oil in the same temperature environment so as to detect changes in the dielectric constant of the lubricating oil independent of the temperature of the oil.

It is another ojbect of the present invention to provide a method and apparatus for comparing the dielectric constant of the lubricating oil of an internal combustion engine with that of unused oil in the same temperature environment with a high degree of resolution in order to determine when the lubricating oil has deteriorated by acquiring a viscosity value predetermined as being too high.

The preferred embodiment of the invention is ideally suited for on-board use in a vehicle since it provides a first capacitive means exposed to the flow of lubricating oil through an internal combustion engine so that its electrical capacitance value is dependent upon the dielectric constant of the lubricating oil flowing therethrough. In addition, a second capacitor means is located so as to be isolated from the flow of the lubricating oil but has its capacitance value determined by the dielectric constant of a reference material. The circuit connected to both the exposed and the isolated capacitor means compares the respective electrical capacitance values and provides an output indicative of the difference therebetween.

BRIEF DESCRIPTION OF THE DRAWINGS

FIG. 1 is a block diagram of the electrical circuit employed in the preferred embodiment of the present invention.

FIG. 2 is an exploded view illustrating the preferred placement of the present invention on an internal combustion engine.

FIG. 3 is a plan view of the spacer component shown in FIG. 2 which embodies the present invention.

FIG. 4 is a plot of output frequency versus wear time accumulated on a lubricating oil utilizing the present invention.

FIG. 5 is a plot of the viscosity of oil measured utilizing conventional methods as a function of wear time accumulated.

DETAILED DESCRIPTION OF THE PREFERRED EMBODIMENT

The present invention is based upon the discovered correlation of viscosity changes in lubricating oil of an engine over time of operation and changes in dielectric constant properties of the oil that accompany the changes in viscosity. Accordingly, the present invention provides a highly sensitive measurement of changes in the dielectric constant of the lubricating oil and an automatic provision for zero referencing the measuring circuit when new oil has been substituted for the used engine oil.

In FIG. 1, a block diagram is presented to illustrate the principles of operation employed in the preferred embodiment. A pair of oscillator circuits 22 and 24 are respectively connected to a sampling capacitor $C_S$ and reference capacitor $C_R$. The sampling capacitor $C_S$ is located within the flow path of the lubricating oil for the internal combustion engine which is being monitored. It is typically an air-gap type capacitor that allows the lubricating oil to pass between the parallel plates thereof and affect the capacitive value of the capacitor $C_S$. Electrical conductors 16 and 18 are connected to the sample oscillator 22 which utilizes the capacitance value at $C_S$ as the variable factor to vary the frequency of the signal output therefrom.

The reference capacitor $C_R$ is similar in value and type to that used as the sampling capacitor $C_S$ but utilizes a dielectric medium, such as unused lubricating oil, as a reference. The reference capacitor $C_R$ is electrically connected to the reference oscillator 24 via conductors 12 and 14 and serves to control the reference frequency output therefrom. The outputs of the sample oscillator 22 and the reference oscillator 24 are fed to a mixer 26, which is shown as a type D flip-flop logic gate with the reference oscillator serving as the clock input and the sample oscillator serving as the input signal. The output from the mixer 26 is the difference frequency between the sample and reference oscillators. The difference frequency signal output from the mixer 26 is passed to a frequency divider circuit 28. In this case, the divider circuit 28 divides by 64. The final output signal from the divider 28 is a square wave signal having a frequency on the order of several hundred hertz that is output to a counter which would typically be employed in a microprocessor circuit so that periodic sampling of the output cycles could be made to determine when the dielectric constant of the lubricating oil has changed sufficiently to warrant an indication to the operator of such oil deterioration.

The circuit shown in FIG. 1 is very similar to the circuit shown in commonly assigned U.S. Pat. No. 4,377,851 (incorporated herein by reference) and was selected because of its sensitivity and stability in comparing capacitance values. The importance of the need for accuracy and stability accompanied by high resolution is due to the observation that the total change in oil dielectric constant only equals approximately 10% over the usable viscosity range of the oil. In addition, one would expect that a useful circuit could resolve the measurement of the dielectric constant to follow the deterioration of the oil and detect a 0.1% change in the oil dielectric constant. The circuit described above performs within the desired performance range.

In the circuit shown in FIG. 1, the sample and reference oscillators and capacitance values $C_S$ and $C_R$ are selected so as to output frequencies in the range of approximately 50 KHz to 75 KHz so that the output from the frequency divider would be no more than 300-500 Hz when the oil is sensed as being deteriorated enough to require replacement.

Experimentally, the sensed change in the sample oscillator frequency, over the total range of change in lubricating oil viscosity, corresponds to an approximate decrease of 5,000 Hz when the sample oscillator operates at about 50 KHz. Hence the necessity to respond to a total change of oil dielectric constant of approximately 10%. However, in order that a difference frequency is continually generated, both oscillator circuits are initially selected to operate around 75 KHz with the reference oscillator being setup to run approximately 30 KHz higher than the sample oscillator when both capacitors are immersed in new oil of the same kind and temperature. Because of these relationships, as the engine oil ages the frequency of the output waveform from the circuitry increases.

Some tests have indicated that the dielectric constant of oil is substantially uniform in the range of approximately 50-100 KHz. Therefore the selection of frequencies to be output from the sample and reference oscillators is fairly noncritical in that range. The aforementioned frequency selections were made by Applicants and employed in the preferred embodiment.

In FIGS. 2 and 3, a spacer device 30 houses the sampling capacitor $C_S$ and the reference capacitor $C_R$ so that they are subject to a common thermal environment. The spacer element 30 is configured to fit between and engine 90 and an oil filter 100 over the threaded oil filter mounting nipple 80. The spacer element 30 is configured to have an aperture 39 which fits over the mounting nipple 80 and a resilience seal (not shown) on the surface abutting the engine block 90. The surface of the spacer 30 that faces the oil filter 100 has a relatively smooth surface onto which the conventional resilient seal of the oil filter is mated. This spacer 30 contains apertures 34, 36 and 38 that allow the oil from the engine to pass through to corresponding apertures in the filter 100. In the aperture 34, the sampling capacitor $C_S$ is mounted and configured to have several parallel plates oriented parallel with the predicted flow of lubricating oil to the filter 100. Electrical leads 16 and 18 extend from the sampling capacitor $C_S$ through sealed plugs 6 and 8, respectively. The plugs 6 and 8 are threadably attached within bores 32 and 34 so that oil does not leak from the spacer 30.

The reference capacitor $C_R$ is an air-gap type capacitor, very similar to $C_S$, and is mounted in a bore 32 having a defined volume within the spacer 30. The capacitor $C_R$ is mounted on a threaded plug 4 and the electrical conductors 12 and 14 are fed through the sealed plug 6 and attached to the capacitor $C_R$. A reference dielectric medium 40 is provided within the volume of the bore 32 and that medium is isolated from the lubricating oil that flows through the sampling capacitor $C_S$ to prevent contamination and aging.

The spacer element 30 is ideally configured of a high thermal conductivity material such as aluminum or other appropriate material that does not react with the contaminants that develope in the oil. With respect to such contaminants, the spacer 30 and the plates of the sampling capacitor $C_S$ may be coated with inert material to protect those items against erosion or other deterioration.

In an actual on-board engine installation, the reference oil 40 would be selected to be unused oil of the same type used as the lubricating oil for the engine. Since the reference oil 40 would remain unused but only be thermally cycled with each operation of the engine, the dielectric constant for the reference capacitor $C_R$ would only vary according to the temperature. On the other hand, the lubricating oil flowing through the sampling capacitor $C_S$ would have additional variations due to the change in its viscosity as the oil deteriorates. The plots in FIGS. 4 and 5 indicate a correlation between laboratory viscosity measurements made on a particular oil sample (Chevron XA6813) after being subjected to accelerated aging in an engine connected to a heavily loaded dynamometer and run at high temperatures.

In FIG. 5, the viscosity of the oil was initially measured at approximately 85 centistrokes. However, the subsequent measurements made at approximately 40° C. indicated a decrease over time prior to increasing at an accelerated rate between 40-60 hours.

In FIG. 4, measurements utilizing the disclosed embodiment of the present invention indicate a correlated reading in frequency of the signal output from the circuit shown in FIG. 1 at an operating temperature of the engine maintained at approximately 110° C. with the viscosity measurements shown in FIG. 4 over the same aging cycle of the engine.

The comparison of the plots in FIGS. 4 and 5 show that the present invention produces signals which provide a correlation to the aging of lubricating oil in an internal combustion engine and may be used in a system that provides warning indications that the oil needs to be restored to its original viscosity condition. Normally this restoration is performed by draining the used engine oil and replacing it with fresh unused oil.

It will be apparent that many modifications and variations may be implemented without departing from the scope of the novel concept of this invention. Therefore, it is intended by the appended claims to cover all such modifications and variations which fall within the true spirit and scope of the invention.

We claim:

1. A system for sensing the condition of the lubricating oil of an engine during engine operation and providing an operator indication when the oil needs to be restored to an acceptable condition, comprising:
   means exposed to the flow of oil through the lubrication system of said engine and having an electrical capacitance value that is dependent on the dielectric constant of said lubricating oil;
   means located so as to be isolated from said flow of lubricating oil but located proximate to said exposed capacitance means so as to be exposed to the same thermal temperatures as said exposed capacitance means and having an electrical capacitance value that is dependent on the dielectric constant of a reference medium that includes a quantity of oil in a predetermined reference volume;
   means connected to said exposed capacitance means and said isolated capacitance means for comparing the respective electrical capacitance values and providing an output signal corresponding to the difference between said capacitance values.

2. A system as in claim 1, which further comprises means for mounting said exposed capacitance means and said isolated capacitance means between the engine and an externally mounted oil filter, wherein said mounting means includes passages, to allow said lubricating oil to flow between said engine and said filter, a sealed volume for containing said isolated capacitance means and said reference oil, and said exposed capacitance means is mounted within a passage to receive the flow of lubrication oil to said filter.

3. A system as in claim 2, wherein said exposed capacitance means is an air gap type capacitor having a plurality of interleaved parallel conductive plates oriented substantially parallel to the predicted flow of lubrication oil to said filter.

4. A system as in claim 2, wherein both said exposed and said isolated capacitance means are air gap type capacitors having a plurality of interleaved parallel conductive plates and said exposed capacitance means has its plates oriented substantially parallel to the predicted flow of lubrication oil to said filter.

5. A system as in claim 3 or 4, wherein said comparing means includes a first oscillator means connected to said exposed capacitance means for generating a sample signal having a frequency that is dependent on the capacitance value of said exposed capacitance means; a second oscillator means connected to said isolated capacitance means for generating a reference signal havig a frequency that is dependent on the capacitance value of said isolated capacitance means; and means connected to receive both said sample and reference signals and output a signal corresponding to the difference in frequency between the sample and reference signals.

6. A system as in claim 1, which further comprises means for mounting said exposed capacitance means and said isolated capacitance means between the engine and an externally mounted oil filter, wherein said mounting means includes passages, to allow said lubricating oil to flow between said engine and said filter, a sealed volume for containing said isolated capacitance means and said reference medium and said exposed capacitance means is mounted within a passage to receive the flow of lubrication oil to said filter.

7. A system as in claim 6, wherein said reference medium of said isolated capacitance means is a quantity of nonflowing oil.

8. A system as in claim 6, wherein said exposed capacitance means is an air gap type capacitor having a plurality of interleaved parallel conductive plates oriented substantially parallel to the predicted flow of lubrication oil to said filter.

9. A system as in claim 8, wherein said reference medium of said isolated capacitance means is a quantity of oil in said sealed volume.

10. A method for sensing the condition of the lubricating oil of an engine during engine operation and providing an operator indication when the oil needs to be restored to an acceptable condition, comprising the steps of:
   exposing a means, having an electrical capacitance value that is dependent on the dielectric constant of said lubricating oil, to the flow of oil through the lubrication system of said engine;
   isolating a means, having an electrical capacitance value that is dependent on the dielectric constant of a reference medium that comprises a quantity of oil in a reference volume, from said flow of lubricating oil; and
   placing said exposed and isolated means in a common thermal environment; and
   comparing the respective electrical capacitance values of said exposed and isolated means and providing an operator indication when said capacitance values differ by more than a predetermined amount.

* * * * *